(12) United States Patent
Kusunoki

(10) Patent No.: US 6,303,583 B1
(45) Date of Patent: Oct. 16, 2001

(54) PHARMACOKINETIC MODULATING CHEMOTHERAPY

(75) Inventor: Masato Kusunoki, 5-30, Kotokucho 4-chome, Nada-ku, Kobe-shi, Hyogo-ken, 657-0025 (JP)

(73) Assignees: Masato Kusunoki, Kobe; Taiho Pharmaceutical Company, Limited, Tokyo, both of (JP)

( * ) Notice: Subject to any disclaimer, the term of this patent is extended or adjusted under 35 U.S.C. 154(b) by 0 days.

(21) Appl. No.: 09/381,287

(22) PCT Filed: Dec. 2, 1998

(86) PCT No.: PCT/JP98/05424

§ 371 Date: Sep. 21, 1999

§ 102(e) Date: Sep. 21, 1999

(87) PCT Pub. No.: WO99/19318

PCT Pub. Date: Apr. 22, 1999

(30) Foreign Application Priority Data

Oct. 9, 1997 (JP) .................................................. 9-277312

(51) Int. Cl.⁷ ............................. A01N 43/04; A61K 31/70
(52) U.S. Cl. ................................... 514/50; 514/49; 514/51
(58) Field of Search ................................... 514/49, 50, 51

(56) References Cited

U.S. PATENT DOCUMENTS 4,914,105 * 4/1990 Fujii et al. .
5,116,900 * 5/1992 Fujii et al. .
5,525,603 * 6/1996 Shirasaka et al. .

OTHER PUBLICATIONS

Fujii et al., Jpn J. Cancer Research, vol. 80, p 509–512 Jun. 1989.*
Japanese Journal of Cancer Research 80, 509–512, Jun. 1989—Fujii et al.
International Journal of Oncology 13: 653–657, 1998—Kusunoki et al.

* cited by examiner

Primary Examiner—James O. Wilson
(74) Attorney, Agent, or Firm—Arent Fox Kintner Plotkin & Kahn, PPLC

(57) ABSTRACT

A method of treating intestinal cancer characterized by performing an adjuvant therapy comprising continuous injection of 5FU and oral administration of UFT in combination with the injection after surgical resection of a human intestinal cancer.

12 Claims, 3 Drawing Sheets

PHARMACOKINETIC MODULATING CHEMOTHERAPY

TECHNICAL FIELD

The present invention relates to a novel adjuvant therapy to be performed after the surgical resection of intestinal cancers such as colorectal cancer and cancer of the small intestine. The term "adjuvant therapy" means an auxiliary therapy.

BACKGROUND ART

With the westernization of dietary habit, patients with cancer of the large intestine are increasing in number among Japanese. It is said that cases of colorectal cancer will exceed those of gastric cancer in number in the 21st century, predominating over other malignant tumors along with lung cancer and breast cancer.

Colorectal cancer is treated by surgical resection, which includes endoscopic polypectomy for early colorectal cancer which is an early carcinoma, and abdominoperineal resection of the rectum, abdominosacral resection of the rectum, pull-through operation, low anterior resection, total pelvic exenteration, Hartmann operation and colostomy for progressive cancers. Radical surgery results in a 5-year survival rate of 50 to 60%. The closer the lesion to the rectum, the higher is the rate of recurrence. The site of recurrence is most frequently local. Distant metastases generally occur to the liver and the lung. The rate of such recurrence or metastasis is about 40% for rectal cancer and about 20% for lung cancer. It is empirically known that the recurrence or metastasis is attributable to the presence of a metastasized lesion not detectable macroscopically or to the spread or dissemination of cancer cells by surgical manipulation. Improvements in the oncologic result of large intestinal cancer are dependent not only on early detection but also on how to prevent recurrence or metastasis after surgical resection. For this purpose, it is general practice to conduct adjuvant therapies including (1) chemotherapy, (2) radiotherapy, (3) immunotherapy, (4) thermotherapy, or (5) other treatment. These therapies are performed singly or in combination pre- or post-operatively or during operation. Among these adjuvant therapies, chemotherapy and radiotherapy are widely performed.

Carter summarized 5-fluorouracil (5FU) administration schedules in an introduction to colorectal cancer, including a method wherein a standard loading dose (SLD) of 370 to 500 mg/m$^2$ bolus (intravenous injection for 5 to 10 min) is given for 5 days, and this dosage regimen is repeated every 4 to 5 weeks. Reportedly, this method achieves effectiveness of 19% (Cancer Treat Rev. 1: 111–129 1974), whereas it is reported that SLD attains effectiveness of 7 to 29% according to research in recent years.

Lokich et al. compared administration of 5FU at a dose of 500 mg/M$^2$ bolus for 5 days every 5 weeks with CVI (continuous intravenous infusion) of the drug at 300 mg/m$^2$/day, reporting that the respective regimens were 7% and 30% in effectiveness, hence a significant difference, but that there was no difference between the resulting survival periods which were 11.2 months and 10.3 months (J. Clin. Oncol. 7: 425–432 1989). Thus, CVI of 5FU over a prolonged period produces an improved effect but still fails to lengthen the survival period.

Various improvements in the dosage regimen of 5FU and research on drugs for use in combination therewith have been made in order to improve such results of treatments. Extensive research has been conducted on therapies comprising CVI of 5FU and use of other anticancer drugs in combination. The drugs to be used in combination with 5FU include Adriamycin, mitomycin C, carmustine, semustine, leucovorin and cisplatin, whereas satisfactory results still remain to be reported.

On the other hand, research has been carried out also on the basis of the therapy comprising CVI of 5FU and use of a multiplicity of drugs in combination with the infusion. Fujii et al. conducted CVI of 5FU in rats implanted with Yoshida sarcoma at a low concentration (20 mg/kg/day) for a prolonged period of time consecutively for 6 days, in combination with oral administration of UFT (to be described later) at a dose of 20 mg/kg once every day, whereby an excellent tumor diminution effect was obtained along with suppressed leukopenia (Jpn. J. Cancer Res. 80, 509–512, 1989).

DISCLOSURE OF THE INVENTION

We have carried out intensive research on dosages and administration schedules so that the basic experiment of Fujii et al. can be practically applied to clinical uses to improve the result of postoperative treatment of intestinal cancer, and consequently found a method of administration which achieves excellent therapeutic results.

The present invention relates to a novel adjuvant therapy to be conducted after surgical resection of intestinal cancer. Stated more specifically, the present invention provides a method of treating intestinal cancer characterized by performing an adjuvant therapy comprising continuous injection of 5FU and oral administration of UFT in combination with the injection after surgical resection of a human intestinal cancer. The term "UFT" refers to an anti-malignant tumor agent comprising a mixture of 1-(tetrahydrofuryl)-5-fluorouracil (brand name: Futraful, common name Tegafur) and uracil in a molar ratio of 1:4. Tegafur is a 5FU derivative corresponding to 5-fluorouracil wherein in a tetrahydrofuryl group is attached to the 1-position thereof and which has its side effect mitigated. Tegafur is given orally or parenterally in the form of suppositories or injections, and releases 5FU to exhibit antitumor activity when metabolized in the liver. On the other hand, UFT is an improved oral antitumor agent of the 5FU type obtained by admixing uracil with Tegafur in a ratio of 4:1, and is widely used in the field of cancer therapies in the U.S., Japan, etc. The therapy of the present invention is applicable to intestinal cancers treated by various surgical operations. The term "intestinal cancers" as used herein refers, for example, to those of the large intestine developing in the cecum, vermiform appendix, ascending colon, transverse colon, descending colon, sigmoid colon, rectum and anal canal, and cancers of the small intestine developing in the duodenum jejunum and ileum.

The therapy of the present invention is a novel adjuvant therapy for patients with an intestinal cancer surgically resected. The therapy is capable of remarkably ameliorating recurrence or metastasis.

The novel adjuvant therapy of the present invention achieves a satisfactory therapeutic result by administering 5FU and UFT to the patient treated by surgical resection, according to the therapeutic schedule of the invention. We named this therapy Pharmacokinetic Modulating Chemotherapy (PMC). The PMC of the invention is performed after surgical resection of a cancer and comprises continuously infusing 5FU intra-arterially or intravenously and orally administering UFT in combination with the infusion. The therapy greatly reduces the incidence of metastasis or local recurrence, leading to survival over a prolonged period.

The intestinal cancer patients to be treated by the therapy of the invention are those developing cancer primarily in the large intestine or small intestine and having the cancerous tissues removed from the primary lesion by surgery. Accordingly, the patients include those having the cancerous tissues removed completely and those having cancer metastasized, for example, to the liver. Continuous infusion is effected by means capable of delivering the drug at a specified rate. Usual drip may be resorted to, while it is desirable to use an external pump permitting adjustment of the rate and duration of infusion. In this case, 5FU is continuously delivered via a catheter adapted for use in surgery and inserted into the blood vessel, by means of a drug infusor attached to one end of the catheter. The catheter may be one widely used in the field of surgery, such as Teflon catheter, polyethylene catheter or the like. The preferred catheter is, for example, 5Fr anthrone P-u catheter (product of Toray Medical Co.). Useful drug infusors are implantable port systems, intravenous infusion pumps and intra-arterial infusion pumps.

Examples of implantable port systems are those usually used insofar as the drug can be continuously delivered intravenously or intra-arterially at a constant rate. For example, MRI port (Bard Access Systems Inc., Salt Lake City, Utah, USA) is desirable. Examples of useful intra-arterial infusion pumps are Watkins chronofusor continuous intra-arterial infusion pump and Sharp continuous intra-arterial infusion pump, MP-22, and Intermate (registered trademark, product of Baxter Healthcare Corporation). Singleday Infusor (product of Baxter Healthcare Corpocation) is desirable as the intravenous infusion pump. 5FU is filled into the implantable port system, and a needle is inserted into the blood vessel in the manner of drip. Alternatively, the drug may be delivered by drip when such infusors are not usable for one reason or another.

The blood vessel to be used for infusion is generally a vein or artery although suitably selectable according to the site of the cancer. Examples of useful veins are the right subclavian vein and cubital vein. Examples of arteries usable are the hepatic artery, gastroduodenal artery, subclavian artery, etc.

It is furthr desirable to perform radiotherapy in order to achieve improved therapeutic results. The radiotherapy is conducted by a common method practiced for treating intestinal cancers. The radiotherapy is conducted prior to, during or after the surgical resection. Preoperative irradiation is especially preferred to ensure wider applicability of surgery and inhibit metastasis or local recurrence.

The method of irradiation to be practiced is one of those usually used for radiotherapy, such as external irradiation and rectal intraluminal brachytherapy. The dose is usually 5 to 70 Gy, preferably 20 to 50 Gy although variable depending on the condition or symptoms. The radiation can be given in a single dose or divided doses.

According to the present invention, an adjuvant therapy is performed which comprises continuous injection of 5FU and oral administration of UFT in combination. More specifically stated, 5FU is continuously injected for a specified period, and UFT is orally given before, during or after the continuous injection.

5FU is used preferably as dissolved in an auxiliary solution for drip, such as saline or a solution of heparin, glucose or fructose. It is especially desirable to deliver 5FU as mixed with 45 ml of saline and 2000 units of heparin using an infusor. 5FU is intra-arterially or intravenously given continuously for 3 to 48 hours, preferably for 6 to 36 hours, more preferably for 12 to 24 hours, once a week as a unit. UFT is orally administered once to four times daily for 3 to 7 days. This dosage regimen is continued for 2 months to 3 years.

The therapy of the present invention is intended to maintain the concentration of 5FU in the blood at a constant level for a prolonged period of time by the continuous infusion of 5FU and the oral administration of UFT. The desired concentration is generally 50 nglm to 400 nglml although variable with the age or symptoms of the patient.

The present invention has achieved remarkable improvements in recurrence rate and prognosis. The improvements in the prognoses of patients are attained especially through a marked reduction of distant recurrences by PMC of the invention. The improvements in prognoses include an improved survival rate, extended survival period, prevention of recurrence and prevention of distant recurrence. It has been found that patients have tolerance for the therapy of the invention, and that 5FU as enhanced by pharmacokinetic modulation is effective for treating tumors.

5FU is given usually at a dose of 100 to 1000 mg/m$^2$/day, preferably about 200 to about 600 mg/m$^2$/day. UFT is given in an amount of up to 3000 mg, preferably about 1000 to about 2800 mg, per week. The daily dose is usually 200 to 600 mg/m$^2$, preferably about 200 to about 300 mg/m$^2$.

According to the invention, it is possible to intravenously and/or orally give other drugs in combination with the oral administration of UFT. Examples of such other drugs usable are leucovorin (LV), cisplatin (CDDP), irinotecan hydrochloride (CPT-11), mitomycin (MMC), methotrexate (MTX), etc.

The patient having a cancerous lesion surgically removed can be treated by the therapy of the invention at home or as an outpatient without hospitalization. The therapy is lower than conventional therapies in medical cost and therefore very useful also from the viewpoint of medical economy.

BEST MODE OF CARRYING OUT THE INVENTION

EXAMPLE 1

Figure 1:
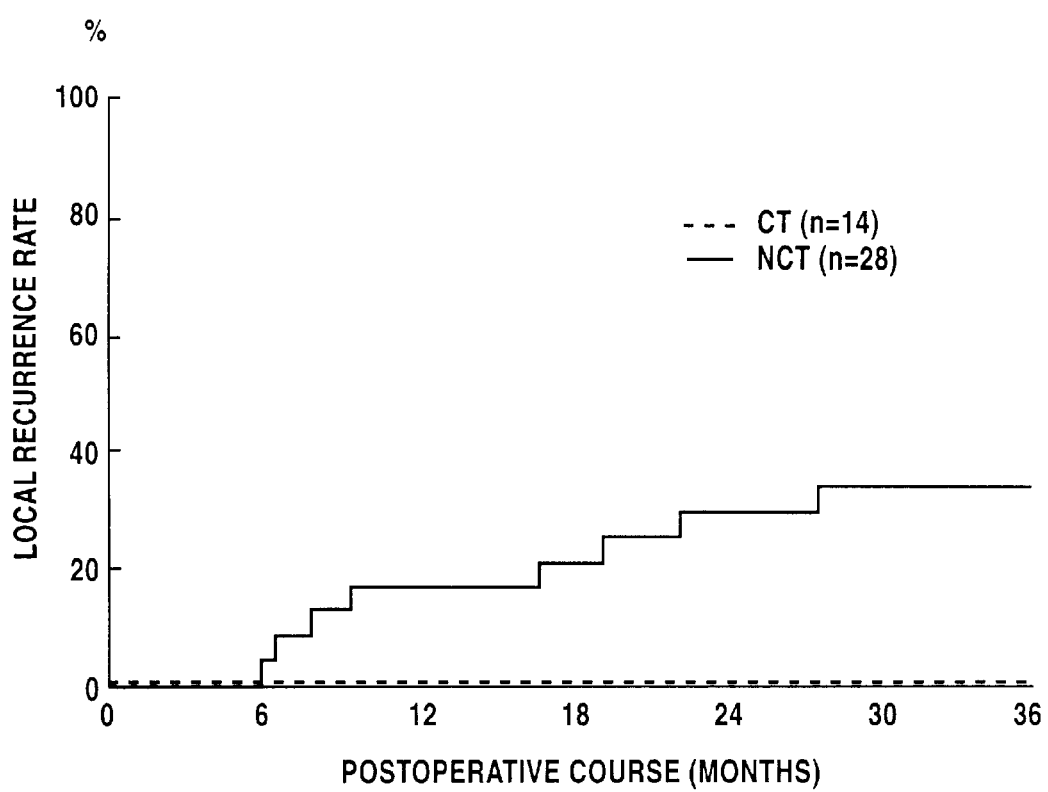
FIG. 1 shows local recurrence curves of two groups, i.e., chemotherapy (CT) group and no-chemotherapy (NCT) group.

One hundred and seven patients with rectal adenocarcinoma in the lower two-thirds of the rectum were treated by preoperative radiotherapy and then by radical resection. All tumors were diagnosed as being primary tumors without distant recurrence and over T2 stage by transrectal ultrasonography prior to radiation. Treatment was conducted for tumors in stage II or III. Resected specimens were examined for p53 (cancer suppressor gene) protein expression. The patients with p53 overexpression, indicating an unfavorable prognosis, were divided into two groups: a chemotherapy (CT) group and a no-chemotherapy (NCT) group.
Radiotherapy Seventy-seven patients were treated with rectal intraluminal brachytherapy (IBT) of 30–70 Gy. Thirty patients underwent preoperative external irradiation (20 Gy delivered in four fractions in one week).

The patients who received chemotherapy underwent catheterization into a subclavian vein (5Fr anthrone P-u catheter, Toray Medical Co.). The catheter was connected to an MRI port (Bard Access Systems Inc., Salt Lake City, Utah, USA). The port was placed in a subcutaneous pocket. An infusion of 5FU (600 mg/m$^2$/24h) mixed with 45 ml saline and heparin (2000 units) was continuously delivered once a week. UFT was orally administered daily. This protocol was started two weeks after surgery and continued for one year.

Immunohistochemical Staining

Three sections from each tumor were selected for p53 staining. Tissue sections of 5 micrometers in thickness were cut off from archived formalin-fixed paraffin-embedded blocks and examined for p53 expression using a standard avidin-blotin complex peroxidase-conjugated streptavidin immunohistochemical staining technique. The staining procedure was described in detail previously. The antibody (RS p53, Nichirei) recognized a mutant p53 with an extended half-life. The level of wild-type p53 was low with a short half-life.

Clinical Assessment

The clinical records of all patients were reviewed. Postoperative follow-up was performed by measuring the serum concentration of carcinoembryonic antigen, X-ray, computed tomography, and ultrasonography. Local recurrence was defined as any tumor recurrence within the pelvis or anal canal. Probability curves for local recurrence, distant recurrence and survival were drawn by the Kaplan-Meier product-limit method. Statistical evaluation was carried out by a log rank test and generalized Wilcoxon test. Significance was assigned to values of $p<0.05$.

There were no hospital deaths among the 107 patients. The overexpression of p53, indicative of a high risk of recurrence, was detected immunohistochemically in 42 of the 107 patients (39%). Of these 42 patients, 32 underwent preoperative IBT (32/77, 42%), and 10 underwent preoperative external irradiation (10/30, 33%). There was no significant difference in the rate of p53 overexpression by radiation method. Fourteen of the 42 patients received an adjuvant chemotherapy, and 28 did not. For the adjuvant therapy, 5FU was intravenously delivered at a dose of 600 mg/m$^2$/day, and 400 mg/day of UFT was given daily in two divided doses every day. This dosage regimen was continued for 6 to 36 months.

Table 1 shows the characteristics of both groups. The total radiation dose in the CT group was significantly lower than that in the NCT group. The percentage of highly malignant tumors in the CT group was significantly higher than that in the NCT group. The median follow-up period in the CT group was 30.8 months, and the patients of the CT group received chemotherapy for at least 6 months. There were no severe chemotherapy-related toxicities (over grade 3). Two of the 14 patients suffered from nausea of diarrhea, but they continued the therapy with a change in the UFT dosage from 400 mg/day to 300 mg/day for 5 days a week.

Figure 2:
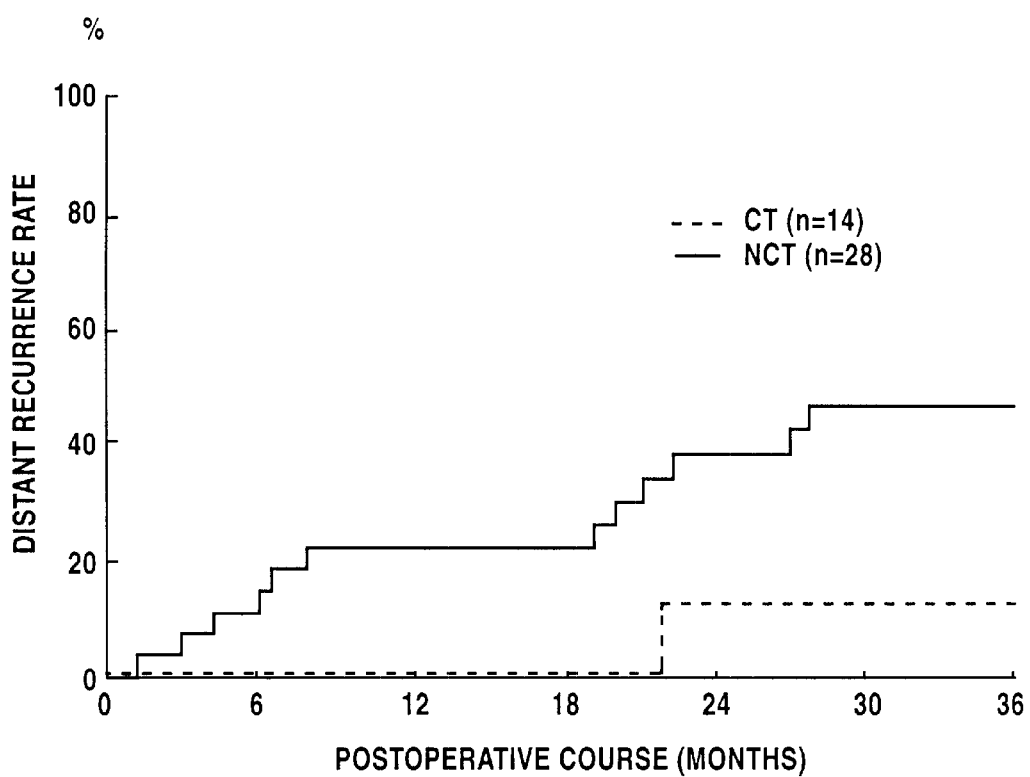
FIG. 2 shows distant recurrence curves of both the CT group and the NCT group.
Figure 3:
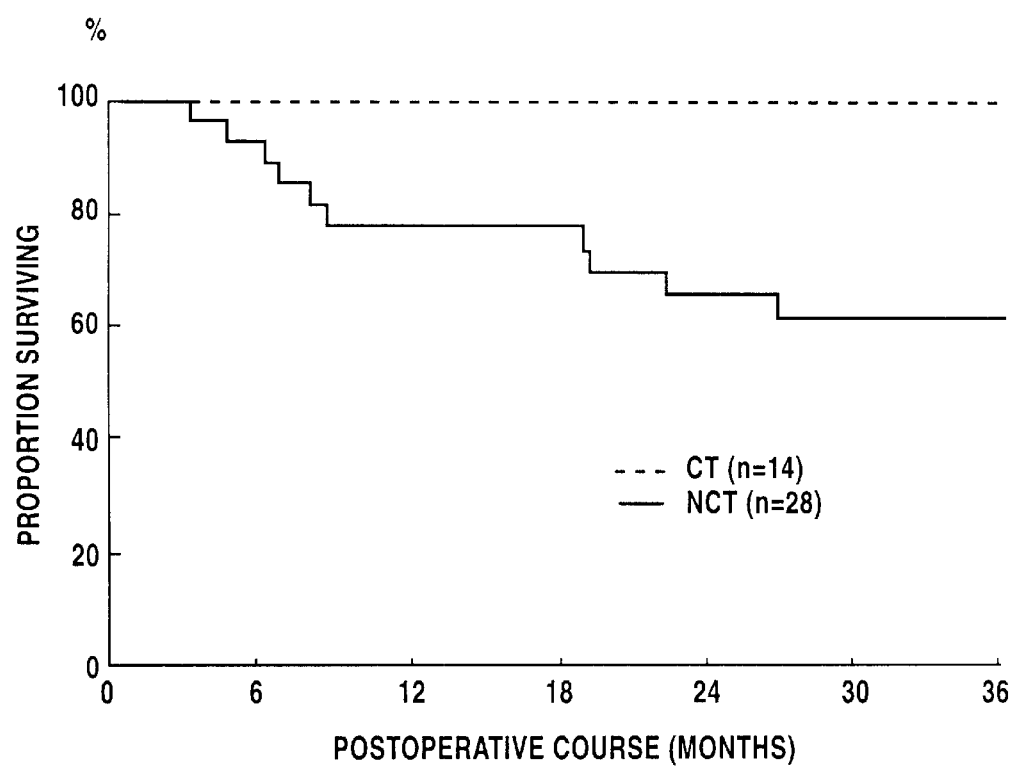
FIG. 3 shows survival curves of both the CT group and the NCT group.

The local and distant recurrence results are summarized in Tables 2 and 3. Local recurrence was observed in none of the 14 patients in the CT group, and in 7 of the 28 patients (28.6%, p=0.0392) in the NCT group. The distant recurrence rate in the CT group was also significantly lower than that in the NCT group ($1/14$=7.1%, $12/28$=42.9%, 7.1% vs. 42.9%, p=0.0376). FIGS. 1 to 3 show the cumulative recurrence curves of the two groups, revealing a significant difference between the groups.

The cumulative 3-year survival rate was 100% in the CT group and 64.3% in the NCT group (p=0.0245). The low distant recurrence rate was associated directly with the high survival rate in the CT group. These prospective analyses indicated that the intravenous infusion of 5FU plus oral UFT improved the prognosis of the patients with p53 overexpression who were considered to be a group with a high risk of recurrence.

TABLE 1

[Characteristics of Rectal Carcinoma Patients with p53 Overexpression]

|  | CT group (n = 14) | NCT group (n = 28) | Significance |
|---|---|---|---|
| Age | 42–78 | 35–80 | NS |
| Average age | 58 | 62 |  |
| Sex (M/F) | 11/3 | 21/7 | NS |
| Preoperative radiation |  |  |  |
| External | 5 | 1 | p = 0.005 |
| Brachytherapy | 9 | 27 |  |
| Radiation dose (Gy) |  |  |  |
| 20 | 5 | 1 | p = 0.005 |
| 30 | 9 | 24 | NS |
| >40 |  | 3 | NS |
| Surgery |  |  |  |
| Sphincter saving resection | 13 | 21 | NS |
| Rectal amputation | 1 | 7 |  |
| Differentiation |  |  |  |
| Well | 2 | 13 | p = 0.045 |
| Moderately | 8 | 14 | NS |
| Poorly | 4 | 1 | p = 0.018 |
| Mucinous | 0 | 0 |  |
| Dukes' classification |  |  |  |
| A | 3 | 3 | NS |
| B | 4 | 7 | NS |
| C | 7 | 18 | NS |
| D | 0 | 0 |  |

TABLE 2

[Pattern of Recurrence after surgery]

|  | CT group (n = 14) | NCT group (n = 28) |
|---|---|---|
| Local only | 0 | 1 |
| Local and distant | 0 | 6 |
| Distant only | 1 | 6 |
| Disease-free survivors | 13 | 15 |

TABLE 3

[Sites of Recurrence after Rectal Carcinoma Surgery]

|  | CT group (n = 14) | NCT group (n = 28) | Significance |
|---|---|---|---|
| Cause of local Recurrence Site |  |  |  |
| Lymph node | 0 | 2 | NS |
| Tumor bed/surgical margin | 0 | 3 | NS |
| Implantation | 0 | 1 | NS |
| Unknown origin | 0 | 1 | NS |

TABLE 3-continued

[Sites of Recurrence after Rectal Carcinoma Surgery]

| | CT group (n = 14) | NCT group (n = 28) | Significance |
|---|---|---|---|
| Site of distant recurrence | | | |
| Liver | 1 | 6 | NS |
| Lung | 0 | 7 | p = 0.040 |
| Peritoneal seeding | 0 | 1 | NS |
| Others | 0 | 1 | NS |

Example 2

Given below are the results achieved by treating patients with various carcinomas.

| | Tumor site | | | | | |
|---|---|---|---|---|---|---|
| Stage | Cecum III | Colon III | Rectum IV | Anus III | Colon III | Small intestine IV |
| Preoperative irradiation | (−) | (−) | (+) | (+) | (−) | (−) |
| Postoperative irradiation | (−) | (−) | (−) | (−) | (−) | (−) |
| Dosage regimen | A | A | C | A | B | D |
| Number of patients | 4 | 24 | 10 | 2 | 6 | 1 |
| Number of 3-yr. survivors | 4 | 23 | 7 | 2 | 6 | 1 |
| 3-yr. survival rate | 100% | 96% | 70% | 100% | 100% | 100% |

Stage II: Metastasis to the lymph node negative, Inovation depth limited within intestinal wall
Stage III: Metastasis to the lymph node positive.
Stage IV: Distant recurrence (metastasis to the liver)

Dosage Regimens

A: Continuous intravenous injection of 5FU for 24 hours once a week, and daily oral administration of UFT twice a day.

B: Continuous intravenous injection of 5FU for 24 hours once a week, and oral administration of UFT twice a day for 5 days per week.

C: Continuous intra-arterial injection of 5FU for 48 hours once a week, and daily oral administration of UFT twice a day.

D: Continuous intravenous injection of 5FU for 24 hours once a week, oral administration of UFT twice a day for 5 days per week, and intravenous injection of 30 mg/w of leucovorin every week in combination with 5FU.

5FU was given at a dose of 600 mg/m$^2$/day, and UFT given in an adjusted amount of 2000 to 2800 mg/week.

INDUSTRIAL APPLICABILITY

The invention achieves improvements in prognoses, such as an improved survival rate, extended survival period, prevention of recurrence and prevention of metastasis to other sites, after cancer treatment.

The patient having a cancerous lesion surgically removed can be treated by the therapy of the invention at home or as an outpatient without hospitalization. The therapy is lower than conventional therapies in medical cost and therefore very useful also from the viewpoint of medical economy.

What is claimed is:

1. A method of treating a human having an intestinal cancer characterized by performing an adjuvant therapy comprising continuous injection of 5-fluorouracil (5FU) for 3 to 48 hours once a week and oral administration of a mixture of 1-(tetrahydrofuryl)-5-fluorouracil and uracil (UFT) one to four times a day for 3 to 7 days per week.

2. A treating method according to claim 1 wherein the intestinal cancer is at least one cancer selected from among cancers of the cecum, vermiform appendix, colon, rectum, anus and duodenum.

3. A treating method according to claim 1 wherein 5FU is continuously injected for a specified period, and UFT is orally given before, during or after the continuous injection.

4. A treating method according to claim 1 wherein the continuous injection of 5FU is continuous intravenous injection.

5. A treating method according to claim 1 wherein the continuous injection of 5FU is continuous intra-arterial injection.

6. A treating method according to claim 3 wherein 5FU is continuously injected intravenously for 3 to 48 hours.

7. A treating method according to claim 3 wherein 5FU is continuously injected intra-arterially for 3 to 48 hours.

8. A treating method according to claim 6 wherein 5FU is continuously injected intravenously for about 6 to about 36 hours once a week, and UFT is orally administered once to four times a day for 3 to 7 days per week.

9. A treating method according to claim 7 wherein 5FU is continuously injected intra-arterially for about 6 to about 36 hours once a week, and UFT is orally administered once to four times a day for 3 to 7 days per week.

10. A treating method according to claim 8 wherein 5FU continuously injected intravenously for about 12 to about hours once a week, and UFT is orally administered once or twice a day for 3 to 7 days per week.

11. A treating method according to claim 9 wherein 5FU continuously injected intra-arterially for about 12 to about 24 hours once a week, and UFT is orally administered once or twice a day for 3 to 7 days per week.

12. A treating method according to claims 1, which is in combination with a preoperative radiotherapy and/or a postoperative radiotherapy.

* * * * *

UNITED STATES PATENT AND TRADEMARK OFFICE
CERTIFICATE OF CORRECTION

PATENT NO.    : 6,303,583 B1
DATED         : October 16, 2001
INVENTOR(S)   : Masato Kusunoki It is certified that error appears in the above-identified patent and that said Letters Patent is hereby corrected as shown below:

<u>Title page,</u>
Please delete the following:

[30]  Foreign Application Priority Data

Oct. 9, 1997    (JP)………………..9-277312

Signed and Sealed this

Thirtieth Day of July, 2002

*Attest:*

*Attesting Officer*

JAMES E. ROGAN
*Director of the United States Patent and Trademark Office*